(12) United States Patent
Karanikolopoulos et al.

(10) Patent No.: US 11,504,333 B2
(45) Date of Patent: Nov. 22, 2022

(54) PHARMACEUTICAL COMPOSITION

(71) Applicant: NOVARTIS AG, Basel (CH)

(72) Inventors: Nikos Karanikolopoulos, Loerrach (DE); Paul Anthony Goulding, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/628,463

(22) PCT Filed: Jun. 29, 2018

(86) PCT No.: PCT/IB2018/054851
§ 371 (c)(1),
(2) Date: Jan. 3, 2020

(87) PCT Pub. No.: WO2019/008487
PCT Pub. Date: Jan. 10, 2019

(65) Prior Publication Data
US 2020/0121607 A1    Apr. 23, 2020

Related U.S. Application Data

(60) Provisional application No. 62/528,779, filed on Jul. 5, 2017.

(51) Int. Cl.
*A61K 9/20* (2006.01)
*A61K 31/506* (2006.01)

(52) U.S. Cl.
CPC .......... *A61K 9/2054* (2013.01); *A61K 9/2018* (2013.01); *A61K 31/506* (2013.01)

(58) Field of Classification Search
CPC .... A61K 31/506; A61K 9/2054; A61K 45/06; A61K 9/2018; A61K 9/0095; A61K 9/10; A61P 35/00
See application file for complete search history.

(56) References Cited

U.S. PATENT DOCUMENTS

| | | | | |
|---|---|---|---|---|
| 7,494,668 B2 * | 2/2009 | Ramalho | ............. | A61K 9/0095 424/464 |
| 2009/0298815 A1 * | 12/2009 | Adams | ................ | C07D 413/04 514/227.8 |
| 2011/0257158 A1 * | 10/2011 | Moschwitzer | .......... | A61P 43/00 514/212.07 |
| 2016/0046615 A1 * | 2/2016 | Lao | ...................... | C07D 417/04 514/275 |

FOREIGN PATENT DOCUMENTS

| | | | | |
|---|---|---|---|---|
| CN | 103751140 A | 4/2014 | | |
| CN | 106539777 A1 | 3/2017 | | |
| WO | 1999025343 A1 | 5/1999 | | |
| WO | 2003028705 A1 | 4/2003 | | |
| WO | 20130093655 A1 | 6/2013 | | |
| WO | WO-2015121649 A1 * | 8/2015 | .......... | A61K 31/437 |
| WO | WO-2016189435 A1 * | 12/2016 | .......... | A61K 9/2009 |

OTHER PUBLICATIONS

Ouellet, Daniele, et al.: "Effects of Particle Size, Food and Capsule Shell Composition on the Oral Bioavailability of Dabrafenib, a BRAF inhibitor, in Patients with BRAF Mutation-Positive Tumors", Journal of Pharmaceutical Sciences, vol. 102, No. 9, Sep. 2013, pp. 3100-3109.

Yakujinippo, [New Product] AFINITOR additional dosage form, Novartis Pharma, Mar. 1, 2013; URL, https://www.yakuji.co.jp/entry30242.html).

Yoichi Ishikawa, et al., Challenge and breakthrough for early development of pediatric preparations, "Regulatory Science Research Group Contributing to early development of Pediatric Drugs", Pharmacology, 2016, vol. 76, No. 5, pp. 324-339.

Yakujinippo, Highlights of Prescribing Information, AFINITOR, Nov. 2013, pp. 1-42.

Yoichi Ishikawa, Highlights of Prescribing Information, CARBAGLU, Mar. 2010, pp. 1-7.

* cited by examiner

*Primary Examiner* — Doan T Phan
(74) *Attorney, Agent, or Firm* — David Cheung

(57) ABSTRACT

The invention pertains to dispersible tablets comprising as active ingredient N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt, processes for preparing the same, and processes for using the same.

15 Claims, No Drawings

PHARMACEUTICAL COMPOSITION

FIELD OF THE INVENTION

The present invention relates to a dispersible tablet for oral suspension comprising N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt, represented by the following formula (I), known as dabrafenib mesylate or Tafinlar® and hereinafter referred to as Compound A:

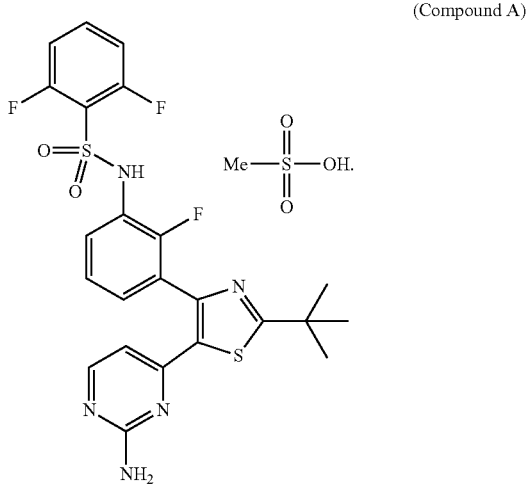

(Compound A)

BACKGROUND OF THE INVENTION

N-{3-[5-(2-Amino-4-pyrimidinyl)-2-(1,1-dimethylethyl)-1,3-thiazol-4-yl]-2-fluorophenyl}-2,6-difluorobenzenesulfonamide (hereinafter Compound B) is a compound which is disclosed and claimed, as a free base, along with pharmaceutically acceptable salts and solvates thereof, as being useful as an inhibitor of BRAF activity, particularly in treatment of cancer, in International Application No. PCT/US2009/042682, having an International filing date of May 4, 2009; International Publication Number WO/2009/137391 and an International Publication date of Nov. 12, 2009, the entire disclosure of which is hereby incorporated by reference. Compound B is the compound of Example 58a.

Compound B can be prepared as described in International Application No. PCT/US2009/042682. Compound B can be prepared as described in United States Patent Publication No. US 2011/0172215, published Jul. 14, 2011, the entire disclosure of which is hereby incorporated by reference.

Suitably, Compound B is prepared in the form of a methanesulfonate salt, or Compound A or dabrafenib mesylate as defined herein. Other suitable pharmaceutically acceptable salt forms of Compound B include sulfate, hydrochloride and sodium salt forms. Salt forms can be prepared by one of skill in the art, for example from the description in International Application No. PCT/US2009/042682 or United States Patent Publication No. US 2011/0172215. Compound A is prepared in Examples 58d-e of United States Patent Publication No. US 2011/0172215.

Solid oral pharmaceutical dosage forms are popular and useful forms of medications for administering pharmaceutically active compounds. A variety of such forms are known, including tablets, capsules, pellets, lozenges, and powders.

However, the formulation of an acceptable solid oral pharmaceutical dosage form on a commercial scale is not straightforward. When administered in vivo, the pharmacokinetic properties of pharmaceutically active compounds may vary substantially depending on the formulation. The formulation must be able to deliver a specific amount of the pharmaceutically active compound sufficient to achieve desired therapeutic drug levels while also minimizing undesirable effects (e.g., toxicity) associated with suboptimal therapeutic drug levels. Moreover, the formulation and process of manufacture must be such as to provide an integral dosage form that maintains its integrity until used. The dosage form must also possess acceptable disintegration and dissolution properties so as to provide the desired profile in use.

Pharmaceutically active compounds, such as Compound A, present particular challenges in preparing high quality dosage forms. While the mesylate salt form has been found to enhance the bioavailability of Compound A, Compound A is a high permeability and a low solubility compound that is very slightly soluble in strongly acidic aqueous media and practically insoluble in slightly acidic, neutral pH, and basic media. The formulator must balance the drug's unique chemical properties with the properties of each excipient in order to prepare a safe, efficacious and easy to use solid oral pharmaceutical dosage form.

Solid dosage forms of Compound A, such as tablets and capsules, are disclosed in International Application No. PCT/US2009/042682. Compound A, in the form of 50 mg and 75 mg capsules, has been approved by the FDA for the treatment of BRAF V600E mutation-positive metastatic melanoma as monotherapy or in combination with trametinib. The combination of Compound A and trametinib has also been approved by the FDA for the treatment BRAF V600E mutation positive metastatic non-small cell lung cancer. The safety and effectiveness of Compound A is currently being evaluated for pediatric treatment of BRAF-mutation positive solid tumors in a recent Phase I study. However, the target doses of Compound A projected for the pediatric patient population may be substantially lower than those afforded by the current capsule formulations.

While tablets and capsules may be acceptable for use in adults, such formulations may be either undesirable or impractical in children or individuals with difficulty swallowing tablets and capsules. In pediatric populations, it is often more desirable to provide a dispersible composition for oral administration, such as a powder or tablet, which can first be dispersed in an ingestible aqueous media, before consumption by the patient. Unlike a powder for oral suspension, a dispersible tablet formulation usually provides shorter reconstitution time for suspension in aqueous media without drug waste.

It would be desirable to provide Compound A in a dispersible solid composition, specifically a pharmaceutical dispersible tablet for oral administration as a suspension (herein also referred to as "dispersible tablet for oral suspension") on a commercial scale that is convenient to administer to children and provides a daily dosage amount of Compound A.

SUMMARY OF THE INVENTION

The present invention is related to a pharmaceutical dispersible tablet for oral suspension of Compound A, which is adapted for reconstitution with water. Additionally, the present invention is related to the method of preparing the dispersible tablet as well as the method of using the dispersible tablet.

DETAILED DESCRIPTION OF THE INVENTION

In one embodiment, the present invention is directed to oral pharmaceutical dosage forms that contain Compound A, preferably the dosage forms are dispersible tablet forms, preferably the dosage forms are produced on a commercial scale.

As used herein, the term "dispersible tablet" means a pharmaceutical formulation in the form of a tablet which is dispersible in an aqueous phase, preferably water, for oral administration as an aqueous suspension.

In one embodiment, the present invention is directed to a dispersible tablet comprising Compound A present in an amount of from 5% to 40% in weight based on the total weight of the tablet.

In one embodiment, the present invention is directed to a dispersible tablet comprising a therapeutically effective amount of Compound A present in an amount of from 5% to 40% in weight based on the total weight of the tablet.

As used herein, the term "improved properties" and derivatives thereof, contemplates several advantages to the pharmacokinetic profile of the in vivo release of Compound A from a dispersible tablet that utilizes an aspect of the present invention when compared to a formulation that does not utilize that aspect of the present invention, suitably the formulation is produced on a commercial scale. Examples of improved properties include: increased oral bioavailability, improved physical and chemical stability, improved photostability, a consistent pharmacokinetic profile, an improved pharmacokinetic profile, a consistent dissolution rate and a stable oral pharmaceutical formulation when the dispersible tablet is mixed with an aqueous vehicle.

Compound A is known to have high permeability and poor aqueous solubility. In water, Compound A forms a supersaturated solution and has the propensity to undergo a rapid, solution-mediated conversion or precipitation to the dabrafenib free base. Delaying the precipitation of Compound A and maintaining a supersaturated solution over an extended period of time is of particular importance to allow for greater absorption in vivo, and results in higher bioavailability of Compound A.

It has been found that the relative bioavailability of Compound A is dependent on the dissolution characteristics of the formulation. In particular, the dissociation rate of capsule formulations of Compound A have been found to be influenced by the presence of hypromellose (HPMC) polymer capsule shell material (Ouellet et. al., J. Pharm. Sci., 102(9): 3100-3109). In vitro dissolution studies comparing gelatin and hypromellose capsule formulations of Compound A showed a higher percentage of dissolution with hypromellose (constituting over 20% of the total weight of the capsule) capsules as compared with gelatin capsules, delaying precipitation of dabrafenib, maintaining a supersaturated solution over an extended period of time, resulting in higher oral bioavailability (Ouellet et. al., J. Pharm. Sci., 102(9): 3105-3107).

In one embodiment, the present invention is also directed to a dispersible tablet comprising:
(a) Compound A,
(b) hypromellose, and
(c) at least one pharmaceutically acceptable excipient suitable for the preparation of dispersible tablets wherein the amount of Compound A or a pharmaceutically acceptable salt thereof, calculated as the percentage of the content in weight of the active moiety based on the total weight of the dispersible tablet, is from about 5% to 40%, preferably about 15% weight based on the total weight of the dispersible tablet; the amount of hypromellose may vary from about 1% to 25%, preferably from about 5% to 10% in weight based on the total weight of the dispersible tablet.

One particular difficulty in the formulation of a dispersible tablet of Compound A is the use of a high level of hypromellose. High levels of hypromellose may negatively impact the dissolution profile in dispersible tablet formulations of Compound A by prolonging tablet disintegration and dispersion time, making the dosage form inconvenient and time-consuming to prepare a sufficiently dispersed aqueous media preparation before administration to the patent. In addition to optimizing hypromellose levels, the selection of disintegrants is crucial to promote the breakup of the tablet in the presence of aqueous media into fine particles.

One or more pharmaceutically acceptable excipients may be present in the dispersible tablets, e.g., those conventionally used, e.g., at least one filler, e.g., lactose, ethylcellulose, microcrystalline cellulose, at least one disintegrant, e.g., cross-linked polyvinylpyrrolidinone, e.g., crospovidone, at least one glidant, e.g., colloidal silicon dioxide, at least one lubricant, e.g., magnesium stearate.

Reference is made to the extensive literature on the subject for these and other pharmaceutically acceptable excipients and procedures mentioned herein, see in particular Handbook of Pharmaceutical Excipients, Eighth Edition, edited by Paul J. Sheskey, American Pharmaceutical Association, Washington, USA and Pharmaceutical Press, London; and Lexikon der Hilfsstoffe far Pharmazie, Kosmetik and angrenzende Gebiete edited by H. P. Fiedler, 4th Edition, Edito Cantor, Aulendorf and earlier editions which are incorporated herein by reference.

Another particular difficulty in the formulation of a dispersible tablet of Compound A is the selection of the disintegrant used to increase the surface area of the product and soften the binding matter that holds together the solid particles of the tablet. At the onset of disintegration, hypromellose may use the free water for its hydration to form a gel and inhibit the water uptake of the disintegrant for wicking (capillary action) or swelling, thereby prolonging tablet disintegration. The phenomenon is even more pronounced with higher levels of hypromellose in the formulation, leading to even longer tablet disintegration time.

Suitable disintegrants according to the invention include but are not limited to starches, celluloses, crosslinked polymers, and effervescent agents, such as corn starch, potato starch, pregelatinized starch, modified corn starch, croscarmellose sodium, crospovidone, sodium starch glycolate, methylcellulose, carboxymethylcellulose and salts thereof such calcium and sodium. In one embodiment of the present invention, the disintegrant is croscarmellose sodium or crospovidone, preferably crospovidone. It has been found that croscarmellose sodium, at high concentrations, can gel and thus increase disintegration time.

The present invention provides dispersible tablets having a disintegration time, e.g., in aqueous media, in water, of not more than 3 minutes, preferably 3 minutes or less, as measured using a disintegration time apparatus, according to the disintegration test of the European Pharmacopoeia 2.9.1 (i.e. disintegration time of tablets in water at 15° C. to 25° C.). Accordingly, the dispersible tablet provides a quick reconstitution time, and, therefore, convenient to administer, e.g., to children. This leads to a better patient compliance By "disintegration time" is meant the time that needs the dispersible tablet to disintegrate in water at 15° C. to 25° C. in a disintegration time device.

The dispersible tablet of the present invention is dispersible in an aqueous phase, preferably water.

The dispersion may be observed visually. Disintegration is considered to be achieved when no residue remains on the screen, or if there is residue, it consists of a soft mass having no palpably firm, unmoistened core, or only fragments of coating (tablets) remain on the screen.

It is known that as tablet hardness of a dispersible tablet increases, disintegration time increases, and friability decreases. Therefore, a short disintegration time is generally demonstrated by relatively soft tablets that potentially lack mechanical robustness (i.e., high friability values). However, tablets with insufficient hardness are liable to crumble, chip or disintegrate before desired (i.e. during packaging, transit, storage or at any time before addition of the tablet to an ingestible aqueous media for consumption.

The present invention aims to provide a dispersible tablet of Compound A with high levels of hypromellose, short disintegration time for convenient suspension reconstitution, and low friability capability to withstand conventional bulk product handing and primary packaging. Surprisingly, it has been found that a formulation comprising Compound A and hypromellose in a total weight of about 1% to 13% in weight based on the total weight of the dispersible tablet, may produce a rapidly dispersing composition that has a disintegration time of not more than 3 minutes, as measured using a disintegration time apparatus, according to the disintegration test of the European Pharmacopoeia 2.9.1 (i.e. disintegration time of tablets in water at 15° C. to 25° C.), and low friability of less than 1% after 100 turns.

As used herein, the term "drug" or "active ingredient" and derivatives thereof, unless otherwise defined, means Compound A or N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt.

As used herein, the term "Compound B" means N-{3-[5-(2-Amino-4-pyrimidinyl)-2-(1,1-dimethylethyl)-1,3-thiazol-4-yl]-2-fluorophenyl}-2,6-difluorobenzenesulfonamide, as the free or unsalted and unsolvated compound. Compound B also refers to the amount of free or unsalted and unsolvated compound in an amount of Compound A.

By the term "commercial scale" and derivatives thereof, as used herein is meant, preparation of a batch scale greater than about 20 kg of direct compression mix, suitably greater than 50 kg, suitably greater than 75 kg or a batch size suitable to prepare at least about 50,000 tablets, suitably at least 75,000 tablets, suitably at least 100,000 tablets.

The term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "effective amount" and derivatives thereof, means that amount of a drug or active ingredient that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Accordingly, the dispersible tablet containing Compound A may be used in the treatment of a neoplasm, particularly a susceptible neoplasm (a cancer or tumor) in a mammal. The present invention also provides a method for treating a neoplasm, particularly a susceptible neoplasm in a mammal in need thereof, which method comprises administering to the mammal a therapeutically effective amount of Compound A in a dispersible tablet of the invention.

"Susceptible neoplasm" as used herein refers to neoplasms which are susceptible to treatment by a kinase inhibitor and particularly neoplasms that are susceptible to treatment by a Raf inhibitor. Neoplasms which have been associated with inappropriate activity of one or more Raf family kinases and particularly neoplasms which are exhibit mutation of a Raf family kinase, overexpression of a Raf family kinase, or mutation of an upstream activator of a Raf family kinase or overexpression of an upstream activator of a Raf family kinase, and are therefore susceptible to treatment with an Raf inhibitor are known in the art, and include both primary and metastatic tumors and cancers. See, Catalogue of Somatic Mutations in Cancer (COSMIC), the Wellcome Trust Sanger Institute, http://www.sanger.ac.uk/genetics/CGP/cosmic/ and those references cited in the background.

Specific examples of susceptible neoplasms within the scope of the invention include, but are not limited to:
  Barret's adenocarcinoma;
  billiary tract carcinomas;
  breast cancer;
  cervical cancer;
  cholangiocarcinoma;
  central nervous system tumors including primary CNS tumors such as glioblastomas, astrocytomas (including glioblastoma multiforme) and ependymomas, and secondary CNS tumors (i.e., metastases to the central nervous system of tumors originating outside of the central nervous system),
  colorectal cancer, including large intestinal colon carcinoma;
  gastric cancer;
  carcinoma of the head and neck including squamous cell carcinoma of the head and neck;
  hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia;
  hepatocellular carcinoma;
  lung cancer including small cell lung cancer and non-small cell lung cancer;
  ovarian cancer;
  endometrial cancer;
  pancreatic cancer;
  pituitary adenoma;
  prostate cancer;
  renal cancer;
  sarcoma;
  skin cancers including melanomas; and
  thyroid cancers.

The foregoing list is intended to disclose each of the recited neoplasms individually. In one particular embodiment, the susceptible neoplasm is a neoplasm which exhibits a mutation in B-Raf.

In another embodiment, there is provided a dispersible tablet of Compound A for use in the treatment of a susceptible neoplasm (e.g., Barret's adenocarcinoma; biliary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers) in a mammal (e.g., human) in need thereof.

By the term "co-administration" as used herein is meant either simultaneous administration or any manner of separate sequential administration of a dispersible tablet containing Compound A, and a further active agent or agents, known to be useful in the treatment of cancer, including chemotherapy and radiation treatment. The term further active agent or agents, as used herein, includes any compound or therapeutic agent known to or that demonstrates advantageous properties when administered to a patient in need of treatment for cancer. As used herein, "further active agent or agents" is used interchangeably with further antineoplastic agent or agents. Preferably, if the administration is not simultaneous, the compounds are administered in a close time proximity to each other. Furthermore, it does not matter if the compounds are administered in the same dosage form, e.g. one compound may be administered by injection and another compound may be administered orally. Suitably, the "co-administration" will consist essentially of a dispersible tablet containing compound A and a second pharmaceutical dosage form containing a further active agent. Suitably, the "co-administration" will consist essentially of a dispersible tablet containing compound A, a second pharmaceutical dosage form containing a further active agent, and a third pharmaceutical dosage form containing another further active agent.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; cell cycle signaling inhibitors; proteasome inhibitors; and inhibitors of cancer metabolism.

Examples of a further active agent or agents (anti-neoplastic agent) for use in combination or co-administered with a presently invented pharmaceutical dosage form, are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer and breast cancer in the United States.

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2)

(salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diamine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-☐-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I—DNA complex. It is believed that cytotoxicity occurs as a result of irreparable double strand breaks caused by interaction of the topoisomerase I: DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b] quinoline-3,14-(4H,12H)-dione monohydrochloride, is commercially available as the injectable solution HYCAMTIN®. Topotecan is a derivative of camptothecin which binds to the topoisomerase I—DNA complex and prevents religation of single strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of Formula A following, including the racemic mixture (R,S) form as well as the R and S enantiomers:

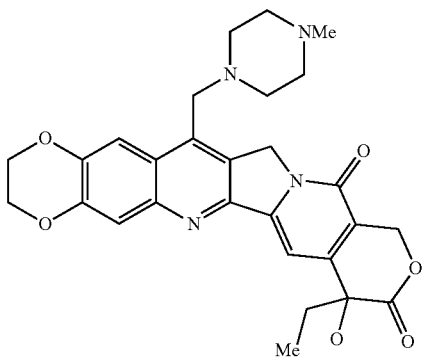

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; and 5,491,237.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5□-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681, 835; 5,877,219; and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidylinositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by overexpression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, PDK1 and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; Pearce, L. R et al. Nature Reviews Molecular Cell Biology (2010) 11, 9-22. and Martinez-lacaci, L., et al, Int. J. Cancer (2000), 88(1), 44-52.

Suitably, the pharmaceutically active compound of the invention is used in combination with a MEK inhibitor. Suitably, N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof, which is disclosed and claimed, in International Application No. PCT/JP2005/011082, having an International filing date of Jun. 10, 2005, the entire disclosure of which is hereby incorporated by reference. N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide can be prepared as described in International Application No. PCT/JP2005/011082

Suitably, the pharmaceutically active compound of the invention is used in combination with an Akt inhibitor. Suitably, N-{(1S)-2-amino-1-[(3-fluorophenyl)methyl] ethyl}-5-chloro-4-(4-chloro-1-methyl-1H-pyrazol-5-yl)-2-thiophenecarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3-fluorophenyl)methyl]ethyl}-5-chloro-4-(4-chloro-1-methyl-1H-pyrazol-5-yl)-2-thiophenecarboxamide is the compound of example 96 and can be prepared as described in International Application No. PCT/US2008/053269. Suitably, N-{ (1S)-2-amino-1-[(3-fluorophenyl)methyl]ethyl}-5-chloro-4-(4-chloro-1-methyl-1H-pyrazol-5-yl)-2-thiophenecarboxamide is in the form of a hydrochloride salt. The salt form can be prepared by one of skill in the art from the description in International Application No. PCT/US2010/022323, having an International filing date of Jan. 28, 2010.

Inhibitors of Phosphotidylinositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody; and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alphav beta3) that will inhibit angiogenesis; endostatin and angiostatin (non-RTK) may also prove useful in combination with the disclosed compounds.

Agents used in immunotherapeutic regimens may also be useful in combination with the compounds of Formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., Progress in Cell Cycle Res., 3: 125 (1997)). Compounds that are known to induce expression of p21WAF1/CIP1 have been implicated in the suppression of cell proliferation and as having tumor suppressing activity (Richon et al., Proc. Nat Acad. Sci. U.S.A. 97(18): 10014-10019 (2000)), and are included as cell cycle signaling inhibitors. Histone deacetylase (HDAC) inhibitors are implicated in the transcriptional activation of p21WAF1/CIP1 (Vigushin et al., Anticancer Drugs, 13(1): 1-13 (January 2002)), and are suitable cell cycle signaling inhibitors for use herein.

Examples of such HDAC inhibitors include:

1. Vorinostat, including pharmaceutically acceptable salts thereof. Marks et al., Nature Biotechnology 25, 84 to 90 (2007); Stenger, Community Oncology 4, 384-386 (2007).

Vorinostat has the following chemical structure and name:

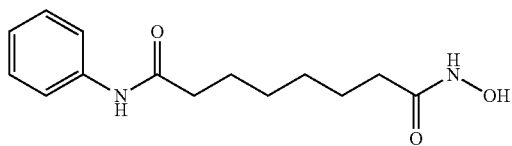 [SMILES: O=C(CCCCCCC(=O)Nc1ccccc1)NO]

N-hydroxy-N'-phenyl-octanediamide

2. Romidepsin, including pharmaceutically acceptable salts thereof. Vinodhkumar et al., Biomedicine & Pharmacotherapy 62 (2008) 85-93.

Romidepsin, has the following chemical structure and name:

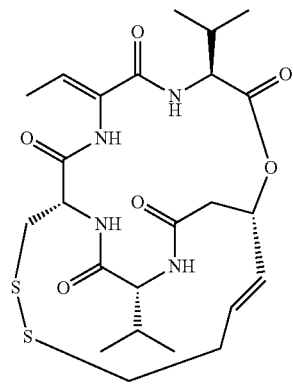 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone 3. Panobinostat, including pharmaceutically acceptable salts thereof. Drugs of the Future 32(4): 315-322 (2007).

Panobinostat, has the following chemical structure and name:

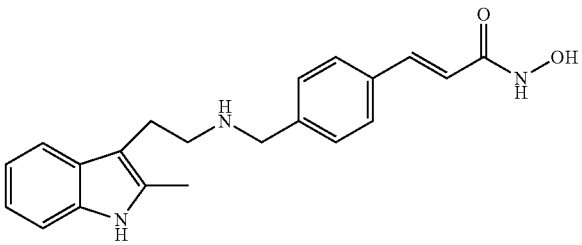 [SMILES: Cc1[nH]c2ccccc2c1CCNCc1ccc(/C=C/C(=O)NO)cc1]

(2E)-N-hydroxy-3-[4-({[2-(2-methyl-1H-indol-3-yl)ethyl]amino}methyl)phenyl]acrylamide 4. Valproic acid, including pharmaceutically acceptable salts thereof. Gottlicher, et al., EMBO J. 20(24): 6969-6978 (2001).

Valproic acid, has the following chemical structure and name:

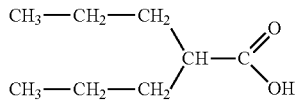

2-propylpentanoic acid

5. Mocetinostat (MGCD0103), including pharmaceutically acceptable salts thereof. Balasubramanian et al., Cancer Letters 280: 211-221 (2009).

Mocetinostat, has the following chemical structure and name:

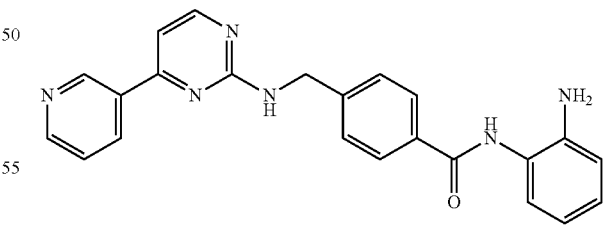

N-(2-Aminophenyl)-4-[[(4-pyridin-3-ylpyrimidin-2-yl)amino]methyl] benzamide

Further examples of such HDAC inhibitors are included in Bertrand European Journal of Medicinal Chemistry 45, (2010) 2095-2116, particularly the compounds of following table therein as indicated below.

Hydroxamic acids
1
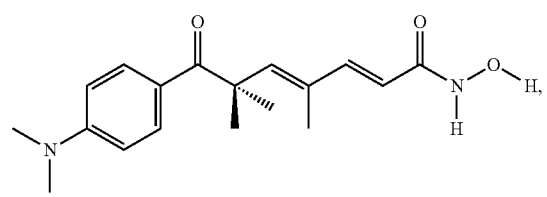
Trichostatine A (TSA)
2
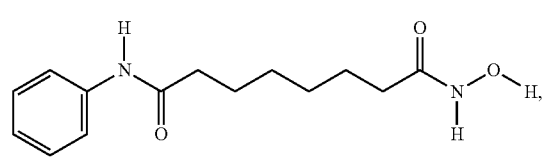
SAHA
3
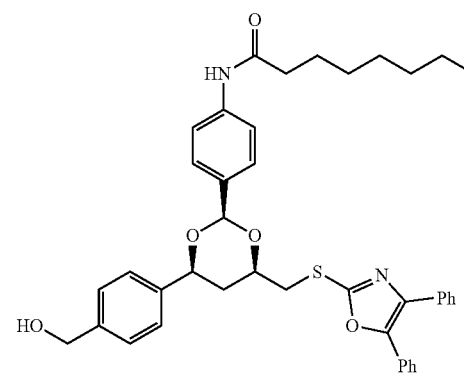
Tubacin
4
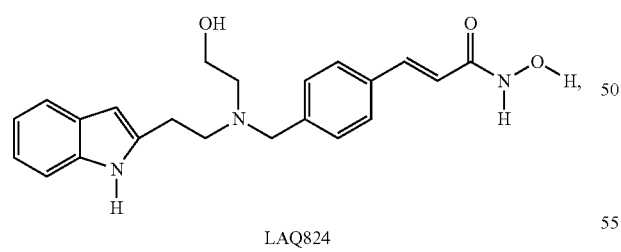
LAQ824
5
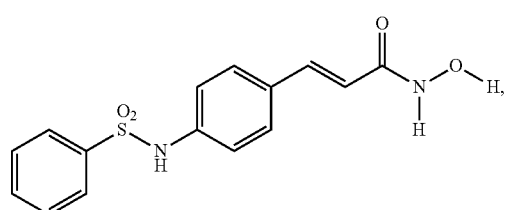
Sulfonamide
6
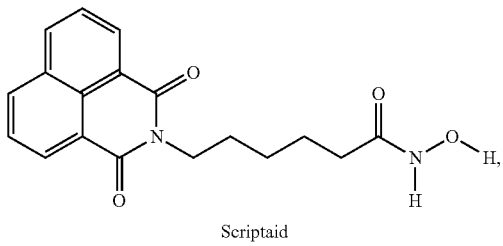
Scriptaid
7
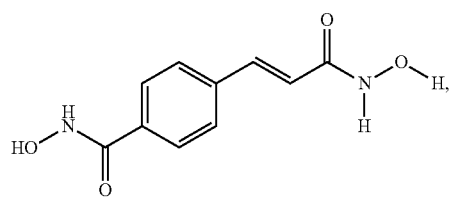
CBHA
8
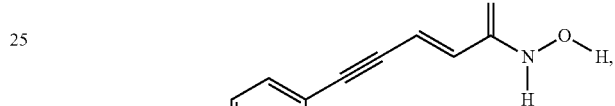
Oxamflatin
Cyclic tetrapeptides
9
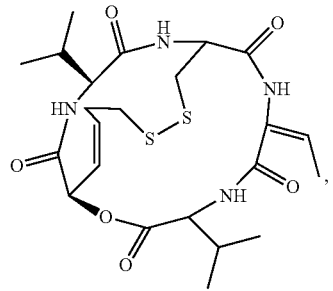
FK228
10
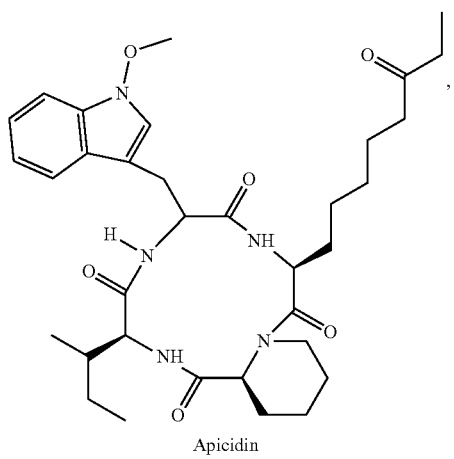
Apicidin -continued Short chain carboxylic acids 11
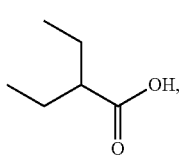
Valproic acid 12
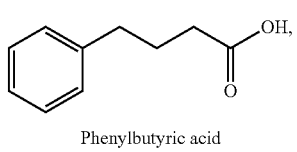
Phenylbutyric acid Benzamides 13
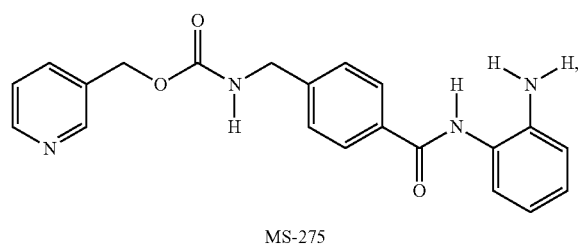
MS-275

14
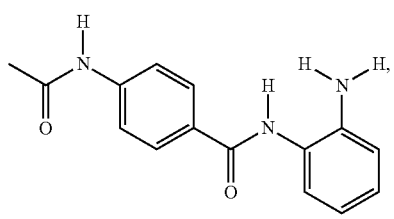
Cl-994

Keto derivatives

15
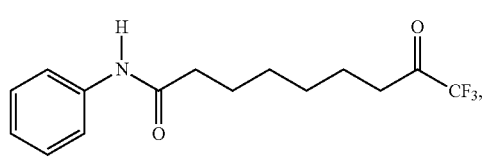
Trifluoromethyl cetone

16
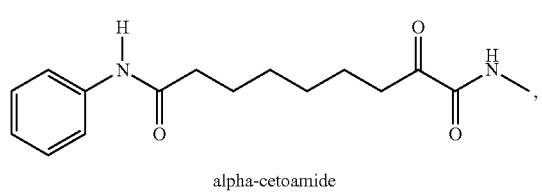
alpha-cetoamide

Proteasome inhibitors are drugs that block the action of proteasomes, cellular complexes that break down proteins, like the p53 protein. Several proteasome inhibitors are marketed or are being studied in the treatment of cancer. Suitable proteasome inhibitors for use herein include:

1. Bortezomib (Velcade®), including pharmaceutically acceptable salts thereof. Adams J, Kauffman M (2004), Cancer Invest 22 (2): 304-11.

Bortezomib has the following chemical structure and name.

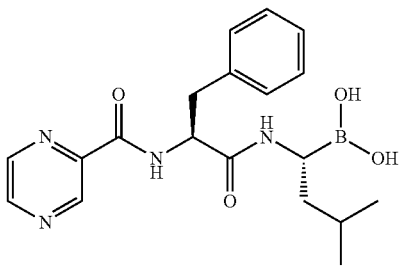 [SMILES: CC(C)C[C@H](NC(=O)[C@H](Cc1ccccc1)NC(=O)c1cnccn1)B(O)O]

[(1R)-3-methyl-1-({(2S)-3-phenyl-2-[(pyrazin-2-ylcarbonyl)amino]propanoyl}amino)butyl]boronic acid 2. Disulfiram, including pharmaceutically acceptable salts thereof. Bouma et al. (1998). J. Antimicrob. Chemother. 42 (6): 817-20.

Disulfiram has the following chemical structure and name.

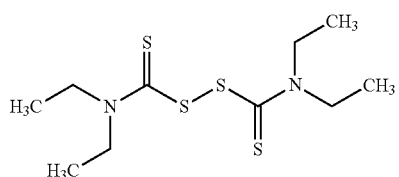

1,1',1'',1'''-[disulfanediylbis(carbonothioylnitrilo)]tetraethane

3. Epigallocatechin gallate (EGCG), including pharmaceutically acceptable salts thereof. Williamson et al., (December 2006), The Journal of Allergy and Clinical Immunology 118 (6): 1369-74.

Epigallocatechin gallate has the following chemical structure and name.

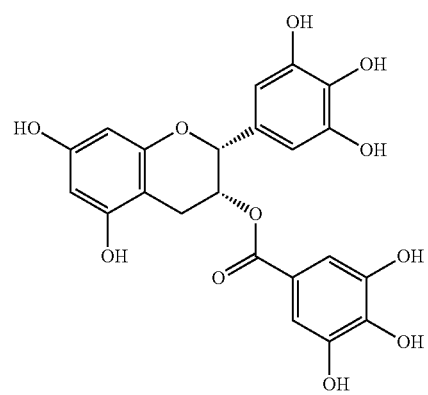 [SMILES: O=C(O[C@@H]1Cc2c(O)cc(O)cc2O[C@@H]1c1cc(O)c(O)c(O)c1)c1cc(O)c(O)c(O)c1]

[(2R,3R)-5,7-dihydroxy-2-(3,4,5-trihydroxyphenyl)
chroman-3-yl]3,4,5-trihydroxybenzoate 4. Salinosporamide A, including pharmaceutically acceptable salts thereof. Feling et at., (2003), Angew. Chem. Int. Ed. Engl. 42 (3): 355-7.

Salinosporamide A has the following chemical structure and name.

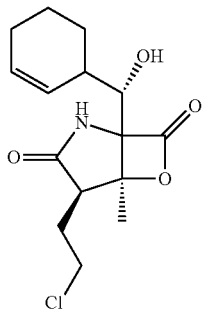 [SMILES: C[C@@]12OC(=O)C1([C@@H](O)C1C=CCCC1)NC(=O)[C@@H]2CCCl]

(4R,5S)-4-(2-chloroethyl)-1-((1 S)-cyclohex-2-enyl
(hydroxy)methyl)-5-methyl-6-oxa-2-
azabicyclo3.2.0heptane-3,7-dione Inhibitors of cancer metabolism—Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models.

D. A. Tennant et. al., Nature Reviews, 2010, 267.

P. Leder, et. al., Cancer Cell, 2006, 9, 425.

Inhibitors of cancer metabolism, including inhibitors of LDH-A, are suitable for use in combination with the formulations of this invention.

Suitable fillers according to the invention include but are not limited to calcium phosphate (e.g., di and tri basic, hydrated or anhydrous), calcium sulfate, calcium carbonate, magnesium carbonate, kaolin, spray dried or anhydrous lactose, cellulose (e.g., microcrystalline cellulose, powdered cellulose), pregelatinized starch, starch, lactitol, mannitol, sorbitol, maltodextrin, powdered sugar, compressible sugar, sucrose, dextrose, and inositol. Fillers that contain little or no water are suitable for tablets of the current invention. In one embodiment of the present invention, the fillers include one or both of mannitol and microcrystalline cellulose.

Suitable glidants according to the invention include but are not limited to silica; colloidal silica, e.g., colloidal silica anhydrous, e.g., Aerosil®, Cab-O-Sil®, and talc, e.g. Luzenac Phama®. In one embodiment of the present invention, the glidant is colloidal silicon dioxide.

Suitable lubricants according to the invention include but are not limited to Mg-, Al- or Ca-stearate, PEG 4000-8000, sodium benzoate, glyceryl mono fatty acid, e.g., having a molecular weight of from 200 to 800 Daltons e.g., glyceryl monostearate (e.g., Danisco, UK), glyceryl dibehenate (e.g., CompritolATO888™, Gattefossé France), glyceryl palmitostearic ester (e.g., Precirol™, Gattefossé France), polyoxyethylene glycol (PEG, BASF), hydrogenated cotton seed oil (Lubitrab, Edward Mendell Co Inc.), castor seed oil (Cutina H R, Henkel). In one embodiment of the present invention, the lubricant is magnesium stearate.

According to the present invention, the amount of filler may vary within a range of from about 35% to 70%, in particular about 65% in weight based on the total weight of the dispersible tablet. The amount of disintegrant may vary within a range of from about 2.5% to 13%, in particular from about 5% to 10% in weight based on the total weight of the dispersible tablet. The amount of hypromellose may vary from about 1% to 13%, in particular from about 5% to 10% in weight based on the total weight of the dispersible tablet. The amount of glidant may vary within ranges of from about 0.1% to 2.5%, in particular from about 0.1% to 0.5% in weight based on the total weight of the dispersible tablet. The amount of lubricant may be from about 0.1% to 2% in weight based on the total weight of the dispersible tablet, preferably from about 0.1% to 1.5%.

In one embodiment of the present invention, the dispersible tablet comprises the following pharmaceutically acceptable excipients: one or more fillers in a total amount of about 65% in weight based on the total weight of the dispersible tablet, hypromellose in a total amount of about 5% to 10% in weight based on the total weight of the dispersible tablet, one or more disintegrants in a total amount of about 5% to 10% in weight based on the total weight of the dispersible tablet, one or more glidants in a total amount of about 0.1% to 0.5% in weight based on the total weight of the dispersible tablet, and/or one or more lubricants in a total amount from about 0.1% to 1.5% in weight based on the total weight of the dispersible tablet.

According to the invention, the process for the preparation of the dispersible tablets comprising of granulating an inner phase, mixing it together with one or more pharmaceutically acceptable excipients and compressing the obtained mixture.

The inner phase comprises Compound A. Preferably, the inner phase comprises Compound A and one or more pharmaceutically acceptable excipients. Preferably, the pharmaceutically acceptable excipients of the inner phase are one or more fillers, one or more disintegrants, hypromellose, and one or more glidants. Preferably, the amount of one or more fillers in the inner phase is ranging from about 5% to 30% in weight based on the total weight of the dispersible tablet, more preferably from about 10% to 25%, and most preferably about 20%. The fillers according to the invention are preferably mannitol and microcrystalline cellulose. The disintegrant is preferably crospovidone. The amount of disintegrant present in the inner phase is preferably less than 10%, more preferably less than 7% in weight based on the total weight of the dispersible tablet. The amount of hypromellose present in the inner phase is preferably less than 10%, more preferably less than 3% in weight based on the total weight of the dispersible tablet. The preferred glidant is colloidal silicon dioxide. The amount of glidant present in the inner phase is preferably ranging from about 0.1% to 1%, preferably less than 0.5% in weight based on the total weight of the dispersible tablet.

The Compound A and hypromellose, one or more fillers, one or more disintegrants, and one or more glidants are mixed together in a blender. After lubrication with magnesium stearate, the mixture is processed for dry granulation, e.g., using roller compaction and a granulating mill.

The outer phase comprises of one or more pharmaceutically acceptable excipients and is mixed with the inner phase using, e.g., a diffusion mixer. Preferably, hypromellose, one or more fillers, and one or more disintegrants are added. Most preferably, mannitol and microcrystalline cellulose are added as fillers in the outer phase. Even more preferably, mannitol is added in the outer phase in the range of about 12% to 45% in weight based on the total weight of the dispersible tablet and microcrystalline cellulose is added in the outer phase in the range of about 8% to 20% in weight based on the total weight of the dispersible tablet. Most preferably, crosspovidone is added in the outer phase as the disintegrant. Even more preferably, crosspovidone is added in the outer phase in the range of about 1% to 5%, more preferably less than 5% in weight based on the total weight of the dispersible tablet.

The outer phase comprising hypromellose, one or more fillers, and one or more disintegrants are mixed together using, e.g., a diffusion mixer, with the granules from the inner phase. After lubrication with magnesium stearate, the final blend is compressed using a suitable rotary press to produce dispersible tablets.

In one embodiment of the invention, the process for the preparation of a dispersible tablet comprises
(a) forming an inner phase comprising
(i) mixing the Compound A together with pharmaceutically acceptable excipients,
(ii) dry-granulating,
(b) forming an outer phase comprising
(i) adding further pharmaceutically acceptable excipients to the inner phase and mixing;
(c) forming the dispersible tablet by
(i) compressing the mixture obtained in step b(i).

More specifically, in one aspect the present invention provides a process comprising:
(i) mixing the Compound A, hypromellose, and pharmaceutically acceptable excipients, e.g., one or more fillers, e.g., mannitol and microcrystalline cellulose, with one or more disintegrants, e.g., Crospovidone, and one or more glidants, e.g., colloidal silicon dioxide, in a diffusion mixer;
(ii) adding to the mixture of one or more lubricants, e.g., magnesium stearate, the mixture is processed for dry granulation, e.g., using roller compaction and a granulating mill and;
(iii) adding hypromellose and pharmaceutically acceptable excipients, e.g., sieved excipients, such as one or more fillers, e.g., mannitol and microcrystalline cellulose, one or more disintegrants, e.g., crospovidone, and mixing, e.g., in a diffusion mixer;
(iv) lubricating the mixture with magnesium stearate;
(v) tabletting the mixture obtained in step (iv) by compression, e.g., in a conventional tablet press, preferably a rotary machine.

By "inner phase" is meant the granulate phase (steps (i) and (ii)) including the active ingredient Compound A and one or more the pharmaceutically acceptable excipients.

By "outer phase" is meant one or more pharmaceutically acceptable excipients added to the inner phase (granulates) (step (iii) and (iv)).

By "total weight of the dispersible tablet" is meant the weight of a tablet being the inner and the outer phase.

The physical and chemical stability may be tested in any conventional manner, e.g., the dispersible tablets may be tested as such by measurement of dissolution, friability, disintegration time, fineness of dispersion, assay for Compound A, degradation products and appearance, e.g., after storage at room temperature, i.e. 25° C./60% RH, and/or storage at 40° C./75% RH.

The dispersible tablets may vary in shape and be, for example, round, oval, oblong, cylindrical or any other suitable shape. In an embodiment of the invention, dispersible tablets obtained by the compression method described above are round or oval. The edges of the dispersible tablets may be beveled or rounded and may be scored. Most preferably, the dispersible tablets are round with biconvex beveled edges.

In an embodiment of the invention, the dispersible tablet comprises from 10 mg to 25 mg dose of Compound A as active ingredient, preferably a 10 mg dose of Compound A as active ingredient.

The dispersible tablet according to the invention is preferably round, biconvex with beveled edges. The dispersible tablet has a diameter ranging between 5 mm and 10 mm, preferably between 5 mm and 7 mm, and more preferably 6 mm.

The hardness, or resistance to crushing, of tablets according to the present disclosure may be determined by standard tests. Tablet hardness is preferably determined according to the standard test specified at European Pharmacopoeia 2.9.8. A device such as a Kraemer® 3S tablet testing device may be used. This test determines the resistance to crushing of tablets, measured by the force needed to disrupt them by crushing.

The dispersible tablets of the invention comprising about a 10 mg dose of Compound A as active moiety may furthermore have a hardness of mean value from about 25 to 75 N, preferably not more than 55 N.

It has been found that formulations comprising Compound A, about 5% to 10% w/w crospovidone, about 5% to 10% w/w hypromellose, wherein hypromellose has nominal viscosity between 4 mPa s to 6 mPa s, preferably 5 mPa s, as measured at 20° C. for a 2% by weight in water, and a 28% to 30% methoxyl substitution or a viscosity of between 80 mPa s to 120 mPa s, preferably 100 mPa s, as measured at 20° C. for a 2% by weight in water, and 19% to 24% methoxyl substitution, and fillers mannitol and microcrystalline cellulose present in a weight ratio of about 2.5:1 to 2:1, may be used to produce a dispersible tablet with a low friability value and a short disintegration time, which complies with the European Pharmacopeia Specifications.

The dispersible tablets of the invention may furthermore be colored and/or marked so as to impart an individual appearance and to make them instantly recognizable. The use of dyes or lake pigments can serve to enhance the appearance as well as to identify the dispersible tablets. The dispersible tablets of the invention may be marked using imprint codes.

The dispersible tablets of the invention are useful for the treatment of BRAF-mutation positive solid tumors.

The activity and characteristics of the dispersible tablets of the invention may be indicated in standard clinical trials and/or animal trials.

Furthermore, the dispersible tablets of the invention obtained are stable both to the production process and during storage, e.g., for 2 years or even 3 years in conventional packaging, e.g., sealed aluminum blister packs. Less than about 5%, e.g., 2 or 3% or less of Compound A as active ingredient may degrade during this time as determined in conventional tests. For example, less than 1% of Compound A as active ingredient is degraded in one year in HDPE filled bottles or blisters.

tion to a patient in need of such therapy which comprises (i) combining the composition with an aqueous medium (ii) allowing the composition to disperse in the aqueous medium to form a dispersion and (iii) ingesting the dispersion.

EXAMPLES

As used herein the symbols and conventions used in these processes, schemes and examples are consistent with those used in the contemporary scientific literature, for example, the Journal of the American Chemical Society or the Journal of Biological Chemistry. Unless otherwise indicated, all temperatures are expressed in OC (degrees Centigrade).

Example 1

TABLE 1

Examples of Dispersible Tablet Compositions

| Ingredient (Pharm. Eur.) | Form 1a | Form 2a | Form 3a | Form 4a | Form 5a | Form 6a |
|---|---|---|---|---|---|---|
| | Quantity [% w/w] per tablet | | | | | |
| Compound A | 14.8 | 14.8 | 14.8 | 14.8 | 14.8 | 14.8 |
| Microcrystalline Cellulose | 19.6 | 21.6 | 17.9 | 19.6 | 21.6 | 19.7 |
| Mannitol | 45.3 | 43.3 | 42.0 | 45.3 | 43.3 | 45.2 |
| Hypromellose 5 mPa s [a] | 5.0 | 7.5 | 10.0 | — | — | — |
| Hypromellose 100 mPa s [b] | — | — | — | 5.0 | 7.5 | 10.0 |
| Crospovidone | 10.0 | 7.5 | 10.0 | 10.0 | 7.5 | 5.0 |
| Acesulfame Potassium | 3.3 | 3.3 | 3.3 | 3.3 | 3.3 | 3.3 |
| Flavor | 0.5 | 0.5 | 0.5 | 0.5 | 0.5 | 0.5 |
| Colloidal Silicon Dioxide | 0.2 | 0.2 | 0.2 | 0.2 | 0.2 | 0.2 |
| Magnesium Stearate | 1.3 | 1.3 | 1.3 | 1.3 | 1.3 | 1.3 |
| Maximum disintegration time | NMT 1 min | NMT 3 min | NMT 3 min | NMT 1 min | NMT 1 min | NMT 3 min |
| Tablet hardness | <55N | <55N | <55N | <55N | <55N | <55N |
| Tablet friability after 100 turns | <0.5% | <0.5% | <0.5% | <0.5% | <0.5% | <0.5% |

[a] Hypromellose polymer with 28%-30% Methoxyl substitution and 7%-12% Hydroxypropoxyl substitution

[b] Hypromellose polymer with 19%-24% Methoxyl substitution and 7%-12% Hydroxypropoxyl substitution The invention relates also to a method of administering to a mammal, preferably a human subject in need of such a treatment, Compound A in the form of a dispersible tablet. The invention also relates to the use of Compound A in the form of a dispersible tablet in the treatment of a mammal, preferably a human subject, for one of the above mentioned diseases or disorders. The invention relates especially to such method wherein a daily dose of 4.5 mg/kg to 5.25 mg/kg of body weight/day of Compound A as active ingredient is administered to a patient. It will be understood that the specific dose level for any particular patient will depend upon a variety of factors including the age, the body weight, general health, drug combination with one or more active drugs, type and severity of the disease.

The medicament package comprises dispersible tablets according to the invention and printed instructions directing that one or more dispersible tablets of Compound A be administered orally.

In another embodiment of the present invention, there is provided a dispersible tablet of Compound A thereof for use in therapy.

In another aspect, the present invention provides a method of administering a pharmaceutical composition of the inven- Dispersible tablets of Compound A, as presented in Table 1, provides a rapidly dispersing compositions that has disintegration time of not more than 3 minutes and low friability of less than 0.5% after 100 turns. Various crospovidone to hypromellose ratios have been tested. Formulations with a lower viscosity hypromellose grade resulted in a longer disintegration time. Formulations with the same hypromellose level (7.5% w/w) and crospovidone level (7.5% w/w) but not the same hypromellose grade in terms of nominal viscosity and methoxyl substitution (Form 2a and Form 5a) resulted in a shorter disintegration time for the higher viscosity hypromellose grade formulation (Form 5a). Formulations with lower hypromellose levels (5% w/w) and higher crospovidone levels (10% w/w) demonstrated similar disintegration time (NMT 1 min), regardless of the viscosity and methoxyl substitution percentage of hypromellose grade used (Form 1a and Form 4a). The influence of hypromellose nominal viscosity on disintegration time appears more pronounced when higher hypromellose levels are used in dispersible tablet formulations of Compound A.

Example 2

Roller compaction, tablets comprising Compound A and the ingredients in Table 1 were prepared.

TABLE 2a

Intra-granular and Extra-granular Dispersible Tablet Compositions

| Ingredient (Pharm. Eur.) | Form 1b | Form 2b | Form 3b | Form 4b | Form 5b | Form 6b |
|---|---|---|---|---|---|---|
|  | Quantity [% w/w] per tablet | | | | | |
| Internal Phase | | | | | | |
| Compound A | 14.81 | 14.81 | 14.81 | 14.81 | 14.81 | 14.81 |
| Microcrystalline Cellulose | 8.13 | 10.28 | 7.13 | 8.13 | 10.28 | 8.44 |
| Mannitol | 12.00 | 10.28 | 10.50 | 12.00 | 10.28 | 12.50 |
| Hypromellose 5 mPa s | 2.50 | 3.75 | 5.00 | — | — | — |
| Hypromellose 100 mPa s | — | — | — | 2.50 | 3.75 | 5.00 |
| Acesulfame Potassium | 3.31 | 3.31 | 3.31 | 3.31 | 3.31 | 3.31 |
| Crospovidone | 6.69 | 5.00 | 6.69 | 6.69 | 5.00 | 3.38 |
| Colloidal Silicon Dioxide | 0.19 | 0.19 | 0.19 | 0.19 | 0.19 | 0.19 |
| Magnesium Stearate | 0.31 | 0.31 | 0.31 | 0.31 | 0.31 | 0.31 |
| Flavor | 0.56 | 0.56 | 0.56 | 0.56 | 0.56 | 0.56 |
| Total | 48.50 | 48.50 | 48.50 | 48.50 | 48.50 | 48.50 |
| External Phase | | | | | | |
| Roller Compaction Granulates | 48.50 | 48.50 | 48.50 | 48.50 | 48.50 | 48.50 |
| Microcrystalline Cellulose | 11.44 | 11.31 | 10.81 | 11.44 | 11.31 | 11.25 |
| Mannitol | 33.25 | 32.94 | 31.38 | 33.25 | 32.94 | 32.63 |
| Hypromellose 5 mPa s | 2.50 | 3.75 | 5.00 | — | — | — |
| Hypromellose 100 mPa s | — | — | — | 2.50 | 3.75 | 5.00 |
| Crospovidone | 3.31 | 2.50 | 3.31 | 3.31 | 2.50 | 1.63 |
| Magnesium Stearate | 1.00 | 1.00 | 1.00 | 1.00 | 1.00 | 1.00 |
| Total | 100.00 | 100.00 | 100.00 | 100.00 | 100.00 | 100.00 |
| Max disintegration time | NMT 1 min | NMT 3 min | NMT 3 min | NMT 1 min | NMT 1 min | NMT 3 min |
| Tablet hardness | <55N | <55N | <55N | <55N | <55N | <55N |
| Tablet friability after 100 turns | <0.5% | <0.5% | <0.5% | <0.5% | <0.5% | <0.5% |

TABLE 2b

Intra-granular and Extra-granular Dispersible Tablet Compositions

| Ingredient (Pharm. Eur.) | Form 1c | Form 4c |
|---|---|---|
|  | Quantity [% w/w] per tablet | |
| Internal Phase | | |
| Compound A | 14.81 | 14.81 |
| Microcrystalline Cellulose | 8.15 | 8.15 |
| Mannitol | 12.05 | 12.05 |
| Hypromellose 5 mPa s | 2.50 | — |
| Hypromellose 100 mPa s | — | 2.50 |
| Acesulfame Potassium | 3.31 | 3.31 |
| Crospovidone | 6.69 | 6.69 |
| Colloidal Silicon Dioxide | 0.19 | 0.19 |
| Magnesium Stearate | 0.31 | 0.31 |
| Flavor | 0.49 | 0.49 |
| Total | 48.50 | 48.50 |
| External Phase | | |
| Roller Compaction Granulates | 48.50 | 48.50 |
| Microcrystalline Cellulose | 11.44 | 11.44 |
| Mannitol | 33.25 | 33.25 |
| Hypromellose 5 mPa s | 2.50 | — |
| Hypromellose 100 mPa s | — | 2.50 |
| Crospovidone | 3.31 | 3.31 |
| Magnesium Stearate | 1.00 | 1.00 |
| Total | 100.00 | 100.00 |
| Max disintegration time | NMT 1 min | NMT 3 min |
| Tablet hardness | <55 N | <55 N |
| Tablet friability after 100 turns | <0.5% | <0.5% |

Process of Making the Tablet

Blending—Sieving—Blending

Components of the inner phase of the tablet are prepared for roller compaction. The Compound A, microcrystalline cellulose, acesulfame potassium, crospovidone, colloidal silicon dioxide, flavor, hypromellose, and mannitol are mixed in a suitably sized blender and blended. The blended material is screened in a suitable sized sieve and transferred into a suitably sized blender and blended.

Magnesium stearate is screened in a suitable sized sieve and transferred to the suitably sized blender containing the blended material and then blended for an additional time Roller Compaction and Milling The lubricated blend is dry granulated into ribbons using a roller compactor. The compacted ribbons are passed through a screen to produce suitably sized granules.

Blending—Sieving—Blending

Components of the outer phase of the tablet are prepared for tabletting. Additional quantities of microcrystalline cellulose, mannitol, hypromellose and crospovidone are mixed in a suitably sized blender and blended. The blended material is screened in a suitable sized sieve and transferred into a suitably sized blender along with the granules of the inner phase and blended. The blend is mixed to combine inner phase and outer phase materials.

Magnesium stearate is screened in a suitable sized sieve and transferred to the suitably sized blender containing the blended material and then blended for an additional time Compression The lubricated blend is compressed on a rotary tablet press fitted with 6 mm round, beveled edged tooling to the target 80 mg weight and to produce 10 mg dispersible tablets. The compressed tablets are sampled for in-process monitoring of individual weight variation, appearance, hardness, thickness, friability and disintegration time.

The tablets are packed into HDPE containers with a desiccant or in blisters (PVC/PVDC backed with a heat sealable lacquered aluminum foil) containing 10 tablets as required.

Example 3

Properties of the 10 mg Dispersible Tablets

| Characteristic | Description |
| --- | --- |
| Shape | Round biconvex beveled edge, 6 mm diameter |
| Average weight | 64-96 mg |
| Hardness | Mean hardness: <55 N |
| Friability | ≤1% after 100 turns |
| Maximum disintegration time | NMT 3 mins (in 900 ml water, 15-25°) |

While the preferred embodiments of the invention are illustrated by the above, it is to be understood that the invention is not limited to the precise instructions herein disclosed and that the right to all modifications coming within the scope of the following claims is reserved.

What is claimed is:

1. A dispersible tablet comprising an inner phase and an outer phase, wherein
    (a) the inner phase comprises:
        (i) N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
        (ii) microcrystalline cellulose;
        (iii) mannitol;
        (iv) hypromellose;
        (v) acesulfame potassium;
        (vi) crospovidone;
        (vii) colloidal silicon dioxide;
        (viii) magnesium stearate; and
    (b) the outer phase comprises:
        (i) microcrystalline cellulose;
        (ii) mannitol;
        (iii) hypromellose;
        (iv) crospovidone;
        (v) magnesium stearate; and
    wherein (I) N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt is present in an amount of from 5% to 40% in weight based on the total weight of the tablet, wherein the tablet contains 10 mg to 25 mg of N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt, (II) hypromellose is present in an amount of from 1% to 13% in weight based on the total weight of the tablet, and (III) mannitol and microcrystalline cellulose are present in an amount of from 35% to 70% in weight based on the total weight of the tablet, wherein mannitol and microcrystalline cellulose are present in a weight by weight ratio of about 2.5:1 to 2:1.

2. The dispersible tablet of claim 1, wherein hypromellose is present in about 5% to about 10% in weight based on the total weight of the tablet.

3. The dispersible tablet of claim 1, wherein hypromellose has nominal viscosity between 4 mPa s to 6 mPa s, as measured at 20° C. for a 2% by weight in water, and a 28% to 30% methoxyl substitution.

4. The dispersible tablet of claim 1, wherein hypromellose has viscosity of between 80 mPa s to 120 mPa s, as measured at 20° C. for a 2% by weight in water, and 19% to 24% methoxyl substitution.

5. The dispersible tablet of claim 1, wherein the tablet has a disintegration time, measured according to the disintegration test of the European Pharmacopoeia 2.9.1, disintegration time of tablets in water at 15° C. to 25° C., of 3 minutes or less.

6. The dispersible tablet of claim 1, wherein the tablet has a hardness of mean value, measured according to the resistance to crushing of tablets test of the European Pharmacopoeia 2.9.8, of not more than 55N.

7. The dispersible tablet of claim 1, wherein crospovidone is present in about 5% to 10% in weight based on the total weight of the tablet.

8. The dispersible tablet of claim 3, wherein:
    (a) the inner phase comprises, by percent weight by total weight (% w/w) of said tablet:
        (i) 14.81% w/w N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
        (ii) 8.13% w/w microcrystalline cellulose;
        (iii) 12.00% w/w mannitol;
        (iv) 2.50% w/w hypromellose;
        (v) 3.31% w/w acesulfame potassium;
        (vi) 6.69% w/w crospovidone;
        (vii) 0.19% w/w colloidal silicon dioxide;
        (viii) 0.31% w/w magnesium stearate; and
    (b) the outer phase comprises, by percent weight by total weight (% w/w) of said tablet:
        (i) 11.44% w/w microcrystalline cellulose;
        (ii) 33.25% w/w mannitol;
        (iii) 2.50% w/w hypromellose;
        (iv) 3.31% w/w crospovidone;
        (v) 1.00% w/w magnesium stearate; and
    wherein hypromellose has viscosity of 5 mPa s, as measured at 20° C. for a 2% by weight in water, and a 28% to 30% methoxyl substitution.

9. The dispersible tablet of claim 3, wherein:
    (a) the inner phase comprises, by percent weight by total weight (% w/w) of said tablet:
        (i) 14.81% w/w N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
        (ii) 10.28% w/w microcrystalline cellulose;
        (iii) 10.28% w/w mannitol;
        (iv) 3.75% w/w hypromellose;
        (v) 3.31% w/w acesulfame potassium;
        (vi) 5.00% w/w crospovidone;
        (vii) 0.19% w/w colloidal silicon dioxide;
        (viii) 0.31% w/w magnesium stearate; and
    (b) the outer phase comprises, by percent weight by total weight (% w/w) of said tablet:
        (i) 11.31% w/w microcrystalline cellulose;
        (ii) 32.94% w/w mannitol;
        (iii) 3.75% w/w hypromellose;
        (iv) 2.50% w/w crospovidone;
        (v) 1.00% w/w magnesium stearate; and
    wherein hypromellose has viscosity of 5 mPa s, as measured at 20° C. for a 2% by weight in water, and a 28% to 30% methoxyl substitution.

10. The dispersible tablet of claim 3, wherein:
(a) the inner phase comprises, by percent weight by total weight (% w/w) of said tablet:
  (i) 14.81% w/w N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
  (ii) 7.13% w/w microcrystalline cellulose;
  (iii) 10.50% w/w mannitol;
  (iv) 5.00% w/w hypromellose;
  (v) 3.31% w/w acesulfame potassium;
  (vi) 6.69% w/w crospovidone;
  (vii) 0.19% w/w colloidal silicon dioxide;
  (viii) 0.31% w/w magnesium stearate; and
(b) the outer phase comprises, by percent weight by total weight (% w/w) of said tablet:
  (i) 10.81% w/w microcrystalline cellulose;
  (ii) 31.38% w/w mannitol;
  (iii) 5.00% w/w hypromellose;
  (iv) 3.31% w/w crospovidone;
  (v) 1.00% w/w magnesium stearate; and
wherein hypromellose has viscosity of 5 mPa s, as measured at 20° C. for a 2% by weight in water, and a 28% to 30% methoxyl substitution.

11. The dispersible tablet of claim 4, wherein:
(a) the inner phase comprises, by percent weight by total weight (% w/w) of said tablet:
  (i) 14.81% w/w N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
  (ii) 8.13% w/w microcrystalline cellulose;
  (iii) 12.00% w/w mannitol;
  (iv) 2.50% w/w hypromellose;
  (v) 3.31% w/w acesulfame potassium;
  (vi) 6.69% w/w crospovidone;
  (vii) 0.19% w/w colloidal silicon dioxide;
  (viii) 0.31% w/w magnesium stearate; and
(b) the outer phase comprises, by percent weight by total weight (% w/w) of said tablet:
  (i) 11.44% w/w microcrystalline cellulose;
  (ii) 33.25% w/w mannitol;
  (iii) 2.50% w/w hypromellose;
  (iv) 3.31% w/w crospovidone;
  (v) 1.00% w/w magnesium stearate; and
wherein hypromellose has viscosity of 100 mPa s, as measured at 20° C. for a 2% by weight in water, and 19% to 24% methoxyl substitution.

12. The dispersible tablet of claim 4, wherein:
(a) the inner phase comprises, by percent weight by total weight (% w/w) of said tablet:
  (i) 14.81% w/w N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
  (ii) 10.28% w/w microcrystalline cellulose;
  (iii) 10.28% w/w mannitol;
  (iv) 3.75% w/w hypromellose;
  (v) 3.31% w/w acesulfame potassium;
  (vi) 5.00% w/w crospovidone;
  (vii) 0.19% w/w colloidal silicon dioxide;
  (viii) 0.31% w/w magnesium stearate; and
(b) the outer phase comprises, by percent weight by total weight (% w/w) of said tablet:
  (i) 11.31% w/w microcrystalline cellulose;
  (ii) 32.94% w/w mannitol;
  (iii) 3.75% w/w hypromellose;
  (iv) 2.50% w/w crospovidone;
  (v) 1.00% w/w magnesium stearate; and
wherein hypromellose has viscosity of 100 mPa s, as measured at 20° C. for a 2% by weight in water, and 19% to 24% methoxyl substitution.

13. The dispersible tablet of claim 4, wherein:
(a) the inner phase comprises, by percent weight by total weight (% w/w) of said tablet:
  (i) 14.81% w/w N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
  (ii) 8.44% w/w microcrystalline cellulose;
  (iii) 12.50% w/w mannitol;
  (iv) 5.00% w/w hypromellose;
  (v) 3.31% w/w acesulfame potassium;
  (vi) 3.38% w/w crospovidone;
  (vii) 0.19% w/w colloidal silicon dioxide;
  (viii) 0.31% w/w magnesium stearate; and
(b) the outer phase comprises, by percent weight by total weight (% w/w) of said tablet:
  (i) 11.25% w/w microcrystalline cellulose;
  (ii) 32.63% w/w mannitol;
  (iii) 5.00% w/w hypromellose;
  (iv) 1.63% w/w crospovidone;
  (v) 1.00% w/w magnesium stearate; and
wherein hypromellose has viscosity of 100 mPa s, as measured at 20° C. for a 2% by weight in water, and 19% to 24% methoxyl substitution.

14. The dispersible tablet of claim 3, wherein:
(a) the inner phase comprises, by percent weight by total weight (% w/w) of said tablet:
  (i) 14.81% w/w N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
  (ii) 8.15% w/w microcrystalline cellulose;
  (iii) 12.05% w/w mannitol;
  (iv) 2.50% w/w hypromellose;
  (v) 3.31% w/w acesulfame potassium;
  (vi) 6.69% w/w crospovidone;
  (vii) 0.19% w/w colloidal silicon dioxide;
  (viii) 0.31% w/w magnesium stearate; and
(b) the outer phase comprises, by percent weight by total weight (% w/w) of said tablet:
  (i) 11.44% w/w microcrystalline cellulose;
  (ii) 33.25% w/w mannitol;
  (iii) 2.50% w/w hypromellose;
  (iv) 3.31% w/w crospovidone;
  (v) 1.00% w/w magnesium stearate; and
wherein hypromellose has viscosity of 5 mPa s, as measured at 20° C. for a 2% by weight in water, and a 28% to 30% methoxyl substitution.

15. The dispersible tablet of claim 4, wherein:
(a) the inner phase comprises, by percent weight by total weight (% w/w) of said tablet:
  (i) 14.81% w/w N-{3-[5-(2-Amino-4-pyrimidinyl)-2-(1,1-dimethylethyl)-1,3-thiazol-4-yl]-2-fluorophenyl}-2,6-difluorobenzenesulfonamide, methanesulfonate salt;
  (ii) 8.15% w/w microcrystalline cellulose;
  (iii) 12.05% w/w mannitol;
  (iv) 2.50% w/w hypromellose;
  (v) 3.31% w/w acesulfame potassium;
  (vi) 6.69% w/w crospovidone;
  (vii) 0.19% w/w colloidal silicon dioxide;
  (viii) 0.31% w/w magnesium stearate; and (b) the outer phase comprises, by percent weight by total weight (% w/w) of said tablet:
  (i) 11.44% w/w microcrystalline cellulose;
  (ii) 33.25% w/w mannitol;
  (iii) 2.50% w/w hypromellose;
  (iv) 3.31% w/w crospovidone;
  (v) 1.00% w/w magnesium stearate; and
wherein hypromellose has viscosity of 100 mPa s, as measured at 20° C. for a 2% by weight in water, and 19% to 24% methoxyl substitution.

* * * * *